United States Patent [19]

Schwartz

[11] Patent Number: 4,780,082
[45] Date of Patent: Oct. 25, 1988

[54] DENTAL ARCH FORM

[76] Inventor: Robert Schwartz, 1271 Westfield Ave., Rahway, N.J. 07065

[21] Appl. No.: 887,253

[22] Filed: Jul. 21, 1986

[51] Int. Cl.⁴ ............................................. A61C 11/00
[52] U.S. Cl. .................................................... 433/213
[58] Field of Search ............... 433/171, 199, 213, 214, 433/74, 179, 54, 200

[56] References Cited

U.S. PATENT DOCUMENTS

| | | | |
|---|---|---|---|
| 452,653 | 5/1891 | Stedman | 433/179 |
| 2,341,155 | 2/1944 | Myerson | 433/214 |
| 2,896,265 | 7/1959 | Chambers | 433/199.1 |
| 3,456,347 | 7/1969 | Spinella . | |
| 3,823,476 | 7/1974 | Hudson et al. | 433/54 |
| 4,059,899 | 11/1977 | Dyal . | |

FOREIGN PATENT DOCUMENTS 845238 7/1952 Fed. Rep. of Germany .

Primary Examiner—Robert Peshock
Attorney, Agent, or Firm—Lerner, David, Littenberg, Krumholz & Mentlik

[57] ABSTRACT

Dental arch forms are disclosed which are adapted to maintain mandibular and maxillary relationship during the fabrication of artificial dentures. The dental arch forms, including mandibular and maxillary members, each include a plurality of teeth luted thereto. An interconnecting device, such as a mating pin and socket is provided on the dental arch forms for interconnecting the mandibular and maxillary members together, whereby the plurality of teeth of these members are aligned in a fixed relationship, which relationship is maintained during fabrication of artificial denture therefrom.

23 Claims, 3 Drawing Sheets

DENTAL ARCH FORM

BACKGROUND OF THE INVENTION

The present invention relates in general to a prefabricated dental arch form, and more particularly, to mandibular and maxillary arch forms having artificial teeth luted thereto. Still more particularly, the present invention is related to an interconnecting arrangement such that the dentition of the mandibular and maxillary arch forms maintain a predetermined occluded relationship, during the fabrication of artificial dentures.

In the usual method for the construction of artificial dentures, the maxillary or mandibular denture is first prepared by placing individual artificial teeth on a base that fits upon either a cast of or the patient's alveolar ridge. Thereafter, the opposing denture, either the maxillary or mandibular denture, is similarly constructed and may be placed in the patient's mouth to check accuracy and asthetics during the construction process. One of the drawbacks of these procedures is that the dentures are built up in a piece meal fashion from individual artificial teeth, with intermediate checks and adjustments.

Accordingly, there is a need for maxillary and mandibular arch forms which are adapted for maintaining the necessary maxillo-mandibular relationship during fabrication of artificial dentures which avoids the disadvantages inherent from the conventional procedures heretofore known.

SUMMARY OF THE INVENTION

In accordance with one aspect of the present invention, there is disclosed dental arch forms comprising a mandibular member including an arch-shaped element and a plurality of mandibular teeth luted thereto, a maxillary member including an arch-shaped element and a plurality of maxillary teeth luted thereto, and interconnecting means provided on the arch-shaped elements of the mandibular and maxillary members for interconnecting the members together, whereby the plurality of teeth of the maxillary members are aligned in a predetermined relationship with the plurality of teeth of the mandibular member.

In accordance with another aspect of the present invention, there is disclosed a dental arch form comprising a mandibular member including a rigid integral arch-shaped element and a plurality of mandibular teeth temporarily luted to a circumferential portion thereof, a maxillary member including a rigid integral arch-shaped element and a plurality of maxillary teeth temporarily luted to a circumferential portion thereof, and interlocking means provided on the arch-shaped elements of the mandibular and maxillary members for interconnecting the members together, whereby the plurality of teeth of the maxillary member is aligned with the plurality of teeth of the mandibular member to maintain a predetermined occluded relationship.

In accordance with another aspect of the present invention, there is disclosed a method of fabricating dentures for a patient comprising the steps of providing a maxillary arch-shaped element having a plurality of maxillary teeth luted thereto, providing a mandibular arch-shaped element have a plurality of mandibular teeth luted thereto, mounting one of the arch-shaped elements to a first cast formed from an impression taken of one of a patient's maxillary or mandibular alveolar ridges, interconnecting the other of the arch-shaped elements to the arch-shaped element mounted to the first cast so as to maintain a predetermined occluded relationship between the maxillary and mandibular teeth, mounting the other of the arch-shaped elements to a second cast formed from an impression taken of the other one of the patient's maxillary or mandibular alveolar ridges, removing the maxillary and mandibular arch-shaped elements leaving the maxillary and mandibular teeth secured to the first and second casts for forming dentures therefrom.

BRIEF DESCRIPTION OF THE DRAWINGS

The above description, as well as further objects, features and advantages of the present invention, will be more fully understood by reference to the following detailed description of a present preferred, but nonetheless illustrative, dental arch form in accordance with the present invention, when taken in conjunction with the accompanying drawings, wherein.

DETAILED DESCRIPTION

Figure 1:
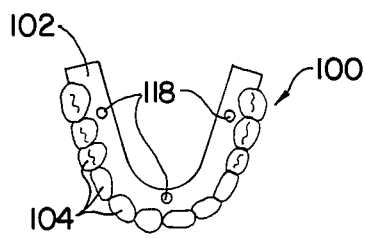
FIG. 1 is a top plan view of a dental arch form constructed in accordance with one embodiment of the present invention, showing an interconnectable arch-shaped element having a plurality of artificial teeth luted thereto.

Referring now to the drawings, wherein like reference numerals represent like elements, there is disclosed in FIG. 1 a prefabricated dental arch form generally designated by referenced numeral 100. The dental arch form is constructed of a rigid arch-shaped element 102 and a plurality of artificial teeth 104 temporarily luted to the circumferential portion of the element. Although only one dental arch form 100 is shown, it is to be understood that a pair of prefabricated dental arch forms are provided in fabricating dentures therefrom, one corresponding to the mandibular set-up and the other corresponding to the maxillary set-up. For illustrative purposes only, the dental arch form 100 shown, will be described as representing the maxillary set-up, which description is equally applicable to the mandibular set-up. Although the dental arch form 100 is shown and described for fabricating full artificial dentures, it is to be understood that such dental arch forms have equal utility in fabricating partial dentures and bridges therefrom.

The arch-shaped element 102 is an integral ridged structure, fabricated from any dimensionally stable material such as thermoplastic or thermosetting materials, olefin polymers, e.g. polyethylene, polyvinylchloride, etc. The arch-shaped element 102 may optionally conform to a standard maxillary or mandibular arch index. The arch-shaped element 102 is preferably anatomically shaped and sized to the alveolar ridge of the patient such that, for example, the central fossa of the individual teeth 104 are aligned over the crest of the alveolar ridge. Ordinary, individual artificial teeth 104 are temporarily attached by, for example, luting, to the arch-shaped element 102 to provide a prefabricated dental arch form 100. All types of cusp teeth, such as steep and flat, may be used and are set in a zero degree plane of occlusion, although a plane of occlusion in the range of from 0° to 45° is also contemplated.

Figure 2:
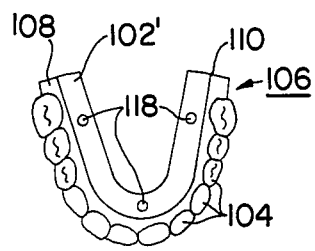
FIG. 2 is a top plan view of a dental arch form, of the type shown in FIG. 1, and constructed in accordance with another embodiment of the present invention.

Turning to FIG. 2, there is disclosed a dental arch form 106 constructed in accordance with another embodiment of the present invention. In this regard, the individual teeth 104 are luted to the arch-shaped element 102′ by means of an intermediate member 108, formed of, for example, low softening point material. The intermediate member 108 permits removal of the arch-shaped element 102 by means of a heated knife or other such implement which is drawn along the mating interface 110.

Figure 3:
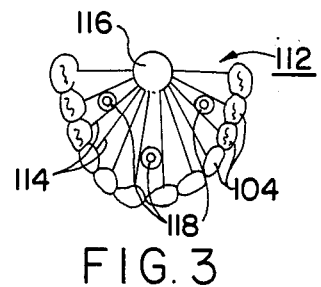
FIG. 3 is a top plan view of a dental arch form, of the type shown in FIG. 1, and constructed in accordance with another embodiment of the present invention.

Turning to FIG. 3, there is disclosed a dental arch form 112 in accordance with another embodiment of the present invention. The teeth 104 are luted to individual spruces 114 extending from a common support 116. The spruces 114 may be formed during an injection molding process from plastic-like material and the like. Although the dental arch form 112 is shown having an individual spruce 114 corresponding to each individual tooth 104, it is contemplated that a lesser number of spruces can be provided, wherein the individual teeth are laterally luted together.

Common to each of the dental arch forms 100, 106, 112, is the provision of a plurality of interconnecting members 118. As shown in FIGS. 1 and 2, the interconnecting members 118 are provided at three spaced-apart locations on the arch-shaped element 102, while being provided between adjacent spruces 114 on the dental arch form 112, as shown in FIG. 3. The interconnecting members 118 may be provided in a lesser or greater number than that disclosed, as well as being provided in other than a triangular relationship as shown. To this end, the purpose of the interconnecting members 118 is to maintain a predetermined relationship between the artificial teeth temporarily luted to the arch form.

Figure 4:
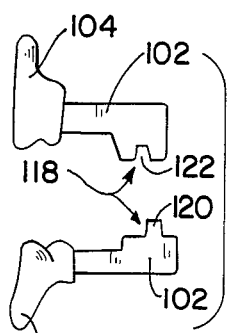
FIGS. 4 through 6 are side elevational views of maxillary and mandibular arch forms, showing their interconnected arrangement to maintain a predetermined occluded relationship.
Figure 5:
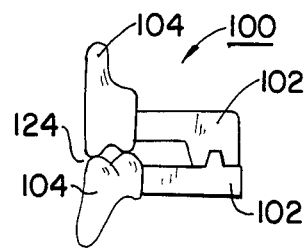
Figure 6:
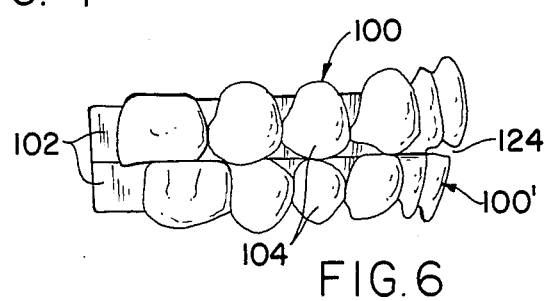
Figure 9:
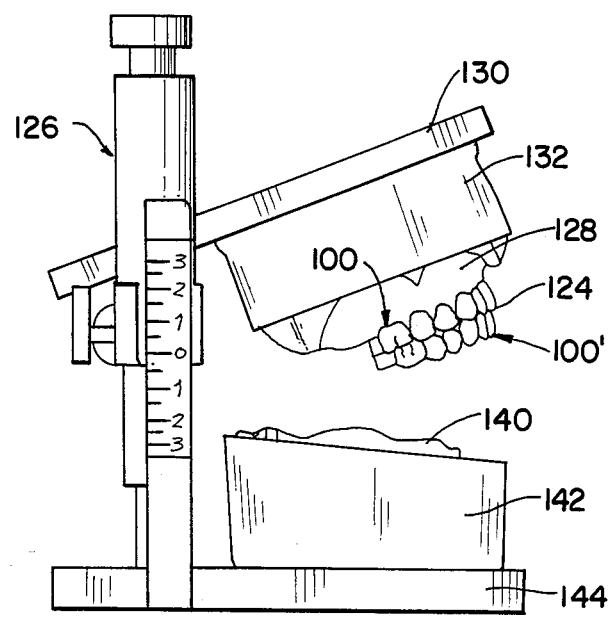
FIGS. 7 through 10 are side elevational views of a dental relator assembly adapted for preparing dentures using the dental arch form of the present invention.

As shown in FIG. 4, the interconnecting members 118 include a projecting pin 120 and socket 122. The pin 120 and socket 122 combination are sized for releasable engagement to permit temporary interconnecting of the mandibular and maxillary set-up formed from the dental arch forms 100 during denture fabrication. As shown in FIGS. 5 and 6, the interconnected dental arch forms 100, forming a mandibular and maxillary set-up, have a predetermined maxillary occlusal relationship. Although the interconnecting members 118 have been described as a pin 120 and socket 122 combination, it is to be understood that other members and devices adapted for interconnecting a pair of dental arch forms 100 together for contemplated. For example, U-shaped clips may be inserted between the teeth 104 and over the arch-shaped elements 102.

The arch forms 100, 106, 112 are used to fabricate dentures and are employed with base plates or casts that are representative of the patient's mandibular and maxillary alveolar ridges. For example, a base plate representative of the patient's mandibular alveolar ridge is mounted on the lower element of a dental articulator. A suitably size mandibular arch form 100 is then adhered to the base plate aligning the artificial teeth 104 as desired on the base plate. The maxillary arch form is interconnected to the mandibular form on the base plate, as shown generally in FIGS. 4–6, achieving the desired occlusion of the mandibular of maxillary artificial teeth. The maxillary base plate is then adhered to the maxillary arch form securing the desired alignment of the maxillary teeth and the patient's maxillary alveolar ridge. The mandibular and maxillary artificial teeth are thus mounted en masse on the patient's base plates rather than individually per traditional practice. Thereafter, arch-shaped element 102 is stripped away from the mandibular and maxillary arch forms leaving the artificial teeth behind on the bases. The resulting assembly, i.e., base plates and artificial teeth, is processed using ordinary methodology to obtain completed dentures.

The fabrication of a mandibular and maxillary set-up from a pair of dental arch forms 100 will now be described with reference to FIGS. 7-10 using, by way of one example only, a dental relator assembly 126 of the type described in U.S. Pat. Nos. 4,155,163 and 3,465,443 issued to the inventor of the subject matter of this application. Initially, an impression is taken of the maxillary and mandibular alveolar ridges of the patient in order to fabricate a corresponding maxillary and mandibular cast, for example, in the manner disclosed in U.S. Pat. No. 4,235,594, also issued to the inventor of the subject matter of this application. As shown in FIG. 8, the maxillary cast 128 is mounted to the undersurface of a maxillary base member 130 of the relator assembly 126 within a flask 132 using, for example, plaster and the like. A prefabricated maxillary dental arch form 100 is selected to conform most closely tot he patient's actual arch size, i.e., anatomically correct. The actual arch size is determined using arch keys and standard maxillary or mandibular arch indexes such as Hawley Arch Charts or Point's Index. In this regard, the selected prefabricated maxillary dental arch forms 100 will place the central fossae of the maxillary teeth 104 over the crest of the maxillary ridge.

Figure 7:
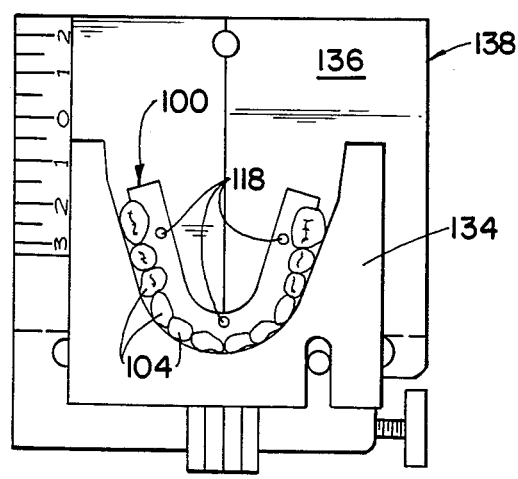
Figure 8:
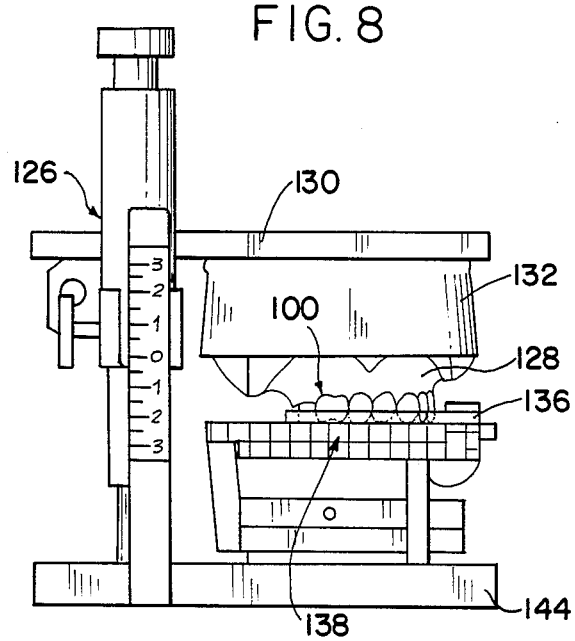
Figure 10:
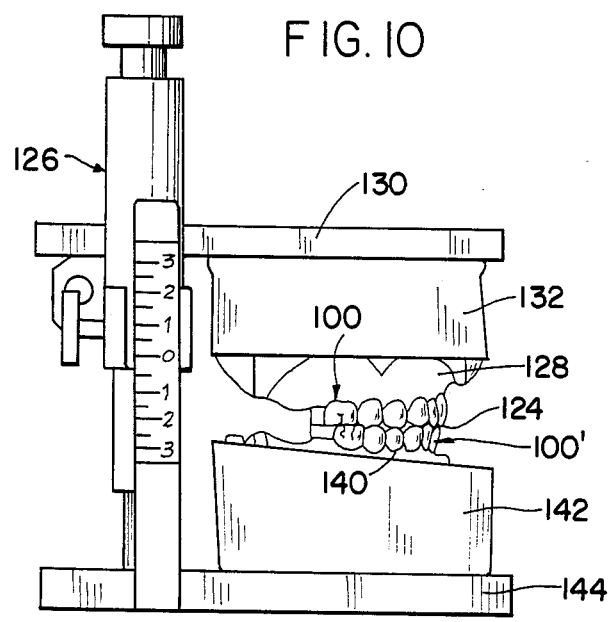

The maxillary dental arch form 100 is positioned within a corresponding arch form templet 134 movably supported on the upper surface 136 of an occlusal base member 138, as shown in FIG. 7. The maxillary base member 130 is brought down to a fully closed position overlying the occlusal base member 138 and the maxillary dental arch form 100 is waxed to the maxillary cast 128 to the desired thickness.

After removing the occlusal base member 138 from the relator assembly 126, the mandibular cast 140 is mounted to the upper surface of a mandibular base member 142 within a flask 144 using, for example, plaster and the like. A prefabricated mandibular dental arch form 100′ is interconnected to the prefabricated maxillary dental arch form 100 by means of the interconnecting members 118. As shown, the maxillary and mandibular dental arch forms 100, 100′ are interconnected to maintain a predetermined occlusion whereby their maxillo-mandibular relationship natural dentition and the proper labial drape. The maxillary base member 130 is again brought down to a fully closed position and the mandibular dental arch form 100′ is waxed to the mandibular cast 140 to the desired thickness. Minor changes may now be made to the mandibular and maxillary dental arch forms 100, 100′ prior to further processing. For example, the individual teeth 104 may be adjusted by, for example, tilting and angling the teeth according to the dictates of good aesthetics.

Where the dental arch form 106 shown in FIG. 2 is used, the arch-shaped element 102' may be removed from the intermediate member 108 using a hot knife manipulated along the interface 110. In the case of the dental arch form 112 shown in FIG. 3, the spruces 114 may be removed using a suitable cutting tool. The resulting mandibular and maxillary dentures are completed using conventional processes, such as deflasking and milling, followed by decasting and polishing.

The use of the interconnected dental arch forms 100, 106, 112, in addition to maintaining the maxillo-mandibular centric relationship, also simplifies the fabrication of dentures when using the relator assembly 126. Previously, it would have been necessary to demount the maxillary cast 128 from the maxillary base member 130 for substitution with the mandibular cast 140 for waxing up the mandibular dental arch form 100'. Thereafter, another demounting step would be required for remounting of the maxillary cast 128 and mandibular cast 140 prior to deflasking and decasting. Thus, the dental arch forms 100, 106, 112 of the present invention greatly simplifies the fabrication of dentures using a relator assembly 126. In addition, it is to be understood that it is not required that a relator assembly 126 be employed for fabricating dentures from the prefabricated dental arch forms 100, 106, 112 of the present invention. That is, as these dental arch forms are provided with interconnecting members 118 to maintain the maxillo-mandibular centric relationship, the wax-up to the maxillary cast 128 and mandibular cast 140 may be attained without the use of a relator assembly 126.

Although the invention herein has been described with reference to particular embodiments, it is to be understood that these embodiments are merely illustrative of the principles and application of the present invention. For example, although the teeth 104 are described as being individual teeth, one or more teeth may be attached together prior to being luted to the arch-shaped element 102. It is therefore to be understood that numerous modifications may be made in the illustrative embodiments and that other arrangements may be devised without departing from the spirit and scope of the present invention as defined by the appended claims.

I claim:

1. Dental arch forms comprising a mandibular member including an arch-shaped element and a plurality of artificial mandibular teeth temporarily luted thereto, a maxillary member including an arch-shaped element and a plurality of artificial maxillary teeth temporarily luted thereto, and interconnecting means and provided on the arch-shaped elements of the mandibular and maxillary members for interconnecting said members together, said interconnecting means comprising a first element provided on said mandibular member and a second element provided on said maxillary member, said first element releasably engageable with said second element to prevent relative movement between said mandibular teeth and said maxillary teeth, whereby said plurality of teeth of said maxillary member are aligned and maintained in fixed relationship with said plurality of teeth of said mandibular member upon engagement of said first element with said second element.

2. The dental arch forms as set forth in claim 1, wherein the arch-shaped elements are of rigid construction.

3. The dental arch forms as set forth in claim 2, wherein the arch-shaped elements are of integral construction.

4. The dental arch forms as set forth in claim 1, wherein said plurality of teeth are luted to a circumferential edge of the mandibular and maxillary members.

5. The dental arch forms as set forth in claim 1, wherein said interconnecting means comprises at least one mating pin and socket therefore.

6. The dental arch forms as set forth in claim 5, wherein said interconnecting means comprises at least three spaced-apart combinations of a mating pin and socket arranged in triangular relationship.

7. The dental arch forms as set forth in claim 1, wherein the arch-shaped elements are formed of thermoplastic material.

8. The dental arch forms as set forth in claim 1, wherein the arch-shaped elements comprise a plurality of spruces individually attached to said plurality of said teeth for maintaining their position relative to one another.

9. The dental arch forms as set forth in claim 1, wherein the arch-shaped elements are formed of thermosetting material.

10. The dental arch forms as set forth in claim 8, wherein said interconnecting means is provided on at least one of said spruces.

11. The dental arch forms as set forth in claim 1, wherein the mandibular and maxillary members further include an intermediate member luting said plurality of teeth to a circumferential portion of said arch-shaped elements.

12. The dental arch forms as set forth in claim 11, wherein the intermediate members are adapted to maintain the position of said plurality of said teeth relative to one another upon removal of the arch-shaped elements.

13. The dental arch forms as set forth in claim 11, wherein said intermediate member is formed of a material adapted to permit separation from the mandibular and maxillary members by manipulation of an implement.

14. Dental arch forms comprising a mandibular member including a rigid integral arch-shaped element and a plurality of artificial mandibular teeth temporarily luted to a circumferential portion thereof, a maxillary member including a rigid integral arch-shaped element and a plurality of artificial maxillary teeth temporarily luted to a circumferential portion thereof, and interconnecting means provided on the arch-shaped elements of the mandibular and maxillary members for interconnecting said members directly together, said interconnecting means comprising a first element provided on said mandibular member and a second element provided on said maxillary member, said first element releasably engageable with said second element to prevent relative movement between said mandibular teeth and said maxillary teeth, whereby said plurality of teeth of said maxillary member are fixedly aligned with said plurality of teeth of said mandibular member to maintain the occluded relationship therebetween upon engagement of said first element with said second element.

15. The dental arch forms as set forth in claim 14, wherein said interconnecting means comprises at least one mating pin and socket therefore.

16. The dental arch forms as set forth in claim 15, wherein said interconnecting means comprises at least three spaced-apart combinations of a mating pin and socket arranged in triangular relationship.

17. The dental arch forms as set forth in claim 14, wherein the mandibular and maxillary members further include an intermediate member luting said plurality of teeth to a circumferential portion of said arch-shaped elements.

18. The dental arch forms as set forth in claim 17, wherein the intermediate members are adapted to maintain the position of said plurality of said teeth relative to one another upon removal of the arch-shaped elements.

19. A method of fabricating dentures for a patient comprising the steps of forming a maxillary arch-shaped element having a plurality of artificial maxillary teeth temporarily luted thereto, forming a mandibular arch-shaped element having a plurality of artificial mandibular teeth temporarily luted thereto, mounting one of said arch-shaped elements to a first cast formed from an impression taken of one of said patient's maxillary or mandibular alveolar ridges, interconnecting the other of said arch-shaped elements directly to the arch-shaped element mounted to said first cast by means of a first element provided on said maxillary arch-shaped element releasably engageable with a second element provided on said mandibular arch-shaped element so as to maintain the occluded relationship and to prevent relative movement between said maxillary and mandibular teeth, mounting the other of said arch-shaped elements to a second cast formed from an impression taken of the other one of said patient's maxillary or mandibular alveolar ridges, removing said maxillary and mandibular arch-shaped elements leaving said maxillary and mandibular teeth secured to said first and second casts for forming dentures therefrom.

20. The method as set forth in claim 19, further including providing said maxillary and mandibular arch-shaped elements of rigid integral construction.

21. The method as set forth in claim 19, further including providing at least one mating pin and socket therefore on said maxillary and mandibular arch-shaped elements for temporarily interconnecting said elements together.

22. The method as set forth in claim 19, further including providing an intermediate member luting said plurality of teeth to a circumferential portion of said maxillary and mandibular arch-shaped elements.

23. The method of claim 22, further including separating said maxillary and mandibular arch-shaped members from said intermediate members by manipulation of an implement therebetween.

* * * * *